United States Patent [19]

McConnell

[11] 4,324,917

[45] Apr. 13, 1982

[54] PREPARATION OF POLYALKYLENE POLYAMINES

[75] Inventor: Thomas T. McConnell, Austin, Tex.

[73] Assignee: Texaco Inc., White Plains, N.Y.

[21] Appl. No.: 182,206

[22] Filed: Aug. 28, 1980

[51] Int. Cl.³ .............................................. C07C 85/06
[52] U.S. Cl. .................................... 564/479; 564/497
[58] Field of Search .......................................... 564/479

[56] References Cited

U.S. PATENT DOCUMENTS 4,036,881  7/1977  Brennan et al. ................. 260/583 P
4,044,053  8/1977  Brennan et al. ................. 260/583 P

FOREIGN PATENT DOCUMENTS 726925  3/1955  United Kingdom ............... 564/479

*Primary Examiner*—John Doll

*Attorney, Agent, or Firm*—Carl G. Ries; Robert A. Kulason; James L. Bailey

[57] ABSTRACT

An improved process for selectively preparing a predominantly noncyclic polyalkylene polyamine compound is disclosed wherein an alkyleneamine compound is contacted with an alkanolamine compound in the presence of a phosphorus-containing cation exchange resin at a temperature of from about 250° C. to about 400° C. under a pressure sufficient to maintain the mixture essentially in liquid phase and the polyalkylene polyamine is then recovered from the resultant reaction mixture. In a preferred embodiment ethylenediamine is contacted with monoethanolamine to produce a predominantly linear polyethylene polyamine product with very low yields of heterocyclic amine materials. The desired polyethylene polyamines produced can be directly recovered from the reaction products by known purification procedures.

8 Claims, No Drawings

PREPARATION OF POLYALKYLENE POLYAMINES

BACKGROUND OF THE INVENTION

1. Field of the Invention

This invention relates to the preparation of predominantly noncyclic polyalkylene polyamine products and more particularly pertains to a liquid phase catalytic process for synthesizing predominantly noncyclic poly(n-alkylene amines) with low heterocyclic amine content.

2. Prior Art

Heretofore, polyalkylene polyamine compounds and particularly polyethylene polyamine compounds such as diethylenetriamine, triethylenetriamine, and the higher homologs as well as the related carbon-substituted homologs have been conventionally produced by reacting an alkyl halide, e.g. ethylene dichloride, with an amine compound such as ammonia, ethylenediamine, and the like at elevated temperatures and pressures. Generally speaking, relatively high yields of predominantly noncyclic polyethylene polyamine compounds are obtained along with varying yields of heterocyclic amines, e.g. piperazine materials. These processes, while generally employed throughout the industry, suffer from serious disadvantages.

Exemplary shortcomings of these procedures include large amounts of energy required to produce reactants and expensive recovery procedures. The resultant hydrohalide salts of ammonia and the polyamines must undergo caustic neutralization to obtain the free polyamines. Separation of the desired free polyamines is difficult and disposal of the polluting by-products, such as the alkali metal halide salt, is expensive. Additionally, the products produced possess undesirable colorants, limiting use of the material in colorcritical applications.

There are several procedures described in the literature for directly preparing predominantly non-cyclic polyethylene polyamines by the condensation reaction of an aminoalkanol compound and an alkylatable amine compound which do not require neutralization of the reaction product to obtain the desired salt-free polyamines.

For example, U.S. Pat. No. 3,714,259 to Lichtenwalter et al describes a catalytic process for the preparation of lower polyethylene polyamines such as diethylenetriamine, whereby an ethyleneamine compound and an ethanolamine compound are contacted in the presence of hydrogen and a hydrogenation catalyst comprised of oxides of nickel, copper, chromium, and like metals, in liquid phase at a temperature of 140° C. to 170° C. This procedure produces only lower polyethylene polyamines. In addition, the reaction requires extended reaction times to provide acceptable conversions. Yet, when the process is carried out under conditions which provide an acceptable conversion rate, selectivity is sacrificed with attendant production of byproducts such as piperazine and piperazine products. The resulting amine product also contains considerable hydroxyl content, another disadvantage.

Another example of a process of this type is disclosed in U.S. Pat. No. 3,121,115 to Meuly. Here certain phosphoric compounds are disclosed effective as catalysts promoting condensation reactions between several types of amines and aminoalkanols generally. The reaction conditions are relatively mild with the process more specifically involving aminoalkylating certain amines having a replaceable amino hydrogen, particularly aromatic primary and secondary amines with an N-tertiary aminoalkanol. The reactants are heated at from 150° C. to 250° C. in liquid phase with continuous water removal in the presence of a phosphoric acid compound. The disclosed process generally requires long reaction times. It is also limited to the use of a N-tertiary aminoalkanol.

Recent greatly improved processes of this type are also disclosed in U.S. Pat. Nos. 4,036,881 and 4,044,053. Here polyalkylene polyamine compounds are made using phosphorus catalysts. By utilizing these processes mixed products having higher non-cyclic concentrations of product are found than heretofore available via prior art processes.

However, it would be a further advantage in the art to discover a process of making polyalkylene polyamines wherein the product amines contained even a higher concentration of non-cyclic compound than found in the prior art discussed above or other previously disclosed processes. Such advantage coupled with the ability to effect the process at relatively high temperatures would be a distinct advantage in the art.

We have now discovered an improved catalytic process whereby predominantly noncyclic polyalkylene polyamines and preferably poly(n-alkylene polyamines) may be produced from the condensation of an alkanolamine compound with an alkyleneamine compound under economically feasible short reaction times. The improved process provides conversion rates of reactants and selectivity comparable to or higher than those obtained by conventional processes which require neutralization with alkali, as described hereinbefore. A great advantage of the process lies in its ability to produce products having a higher concentration of noncyclic products than heretofore could be achieved. Surprisingly, it has been discovered that the condensation reaction may be carried out under rather severe processing conditions, such as temperature above about 250° C. in liquid phase without any decomposition of the catalyst involved here or products.

SUMMARY OF THE INVENTION

In accordance with the broader aspects of the instant invention, predominantly noncyclic polyalkylene polyamines are selectively produced directly from an alkyleneamine compound and alkanolamine compound by a process which includes contacting the alkyleneamine compound with the alkanolamine compound in the presence of a cation exchange resin containing active phosphorus sites acting as a catalyst at temperatures of from about 250° C. to about 400° C. under a pressure sufficient to maintain the mixture essentially in liquid phase. The polyalkylene polyamines thus produced are then recovered from the resultant reaction mixture.

In accordance with one embodiment, an n-alkylene diamine or high homolog having two primary terminal amino groups is contacted with the corresponding n-alkanolamine having a single primary hydroxy group and a terminal primary amino group to produce higher homologs of the n-alkylene polyamine reactant.

In accordance with a preferred embodiment, ethylenediamine is contacted with monoethanolamine to produce predominantly noncyclic polyethylene polyamines such as diethylenetriamine, triethylenetetramine, tetraethylenepentamine and the like.

DESCRIPTION OF THE PREFERRED EMBODIMENT

Briefly, the present invention is an improved process for synthesizing predominantly noncyclic polyalkylene polyamines and preferably linear polyethylene polyamines such as diethylenetriamine and higher homologs. The inventive process involves contacting an alkyleneamine having primary amino groups, and preferably having an unbranched alkylene moiety such as ethylenediamine, with an alkanolamine having a primary or secondary hydroxy moiety and a primary amine and preferably having an unbranched alkylene moiety in the presence of a phosphorus-containing cation exchange resin. The reactants are contacted at a temperature of from above about 250° C. to about 400° C. under a pressure sufficient to maintain the reaction mixture essentially in liquid phase. The predominantly noncyclic polyethylene-polyamines produced are recovered directly such as by conventional distillation techniques in high quality yields without any requirement of neutralization by the addition of alkali. The process provides acceptable conversion levels under relatively short reaction times, usually about one-half to 5 hours. Unexpectedly, formation of cyclic products, such as piperazine compounds, and excessively branched by-products is comparable to or below the amount normally obtained in conventional procedures for preparing polyethylene polyamines where neutralization procedures are required.

Generally, the polyalkylene polyamines that are produced in accordance with the instant invention can be depicted by the formula:

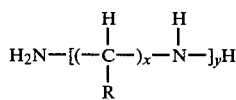

wherein R is hydrogen or a lower alkyl radical, x is a number from 2 to about 6; and y is a number from 2 to about 6. Examples of such compounds are dipropylenetriamine, tributylenetetramine, di-2-methylethyltriamine, tri-2-ethylethylenetetramine and the like. This list is exemplary and not meant to be exhaustive of the polyalkylene polyamine compounds that can be formed.

The most preferred polyalkylene polyamine is a polyethylene polyamine of the above formula wherein R is hydrogen, x is 2 and y is a number from 2 to about 5. Examples of such compound is diethylenetriamine, triethylenetetramine, tetraethylenepentamine and the like.

The alkanolamine compounds which can be generally employed in the present invention include those represented by the formula:

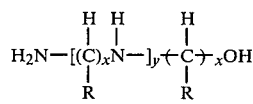

wherein R is hydrogen or a lower alkyl radical; x is a number from 2 to about 6; and y is a number from 0 to about 3. The most preferred alkanolamine is an ethanolamine of the above formula wherein R is hydrogen, x is 2 and y is 0 to 3. Examples of such compounds are monoethanolamine, N-(2-aminoethyl)ethanolamine, etc.

The alkyleneamine reagent that can be used in accordance with the instant invention can be depicted by the general formula:

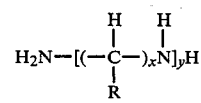

wherein R is a hydrogen or lower alkyl radical, X is a number from 2 to about 6, and y is a number of from 1 to 4. The most preferred alkyleneamine reagent is ethylenediamine.

Any cation exchange resin containing active phosphorus sites may be used here to act as a catalyst. Such phosphorus-containing cation exchange resins are well known in the art and need little elaboration. The cation exchange resins provides exchangable phosphorus-containing ions such as phosphonous, phosphonic, phosphoric, and phosphorous.

In somewhat more detail the resins useful here are weak-acid cation exchange resins containing one or more of the above phosphorus-containing exchangeable ions. The cation exchanges of this type are typically made by copolymerizing divinylbenzene with a comonomer containing the above phosphorus-type groups. In yet another synthesis styrenedivinyl copolymers may be made, chloromethalated, and then the halomethyl groups further reacted with phosphorus-containing molecules. Thus, for example, phosphonic acid groups may be introduced into cross-linked polymers containing halomethyl groups by reaction with an ester of phosphorous acid. Typical resins of this type are set out in British Pat. No. 726,925.

Duolite resins available from Diamond Alkali Co. are typical commercial phosphorus-containing resins. Examples of these are Duolite ES-62, Duolite ES-63, and Duolite ES-65 which are the phosphonous, phosponic and phosphoric acid types, respectively.

According to a greatly preferred embodiment, monoethanolamine and ethylenediamine are intimately contacted by admixing. The admixture is then heated in the presence of the cation exchange resin catalyst at a temperature of from about 250° C. to about 350° C. and perferably at a temperature of about 275° C. to about 325° C., under a pressure sufficient to maintain the reaction mass in liquid phase which normally ranges from about 200 to about 2,500 psig. The reaction is allowed to proceed at the temperature employed until the desired amount of conversion is obtained. Preferably the reaction is carried out under such conditions for a time period sufficient to provide a total reactants conversion of from about 10% to about 75% which is usually within the range of about 0.5 to about 5.0 hours.

The ethylenediamine and the monoethanolamine are utilized in molar ratios of from about 1:2 to about 5:1. Preferably, the molar ratio is about 1:1 to about 2:1.

Generally the process of the invention can be carried out batchwise or continuously employing well-known batch and continuous processing techniques and conventional processing apparatus. Where the process is carried out continuously, it is preferred to employ space velocities of reactants of from about 0:1 to about 4, and preferably from about 0.5 to 1.5, grams total reactants per milliliter of total reactor volume per hour. The cation exchange resins are usually employed as a fixed bed catalyst in the batch or continuous reactor system.

It is critical to control the amount of water of reaction present during the heating of reactants and catalyst, such as by removal thereof as it is formed. Usually, it is preferred to retain the water in the reaction zone and remove it from the reaction mass during recovery of the predominantly noncyclic polyalkylene polyamines.

The desired main non-cyclic polyalkylene polyamine compounds may be readily recovered from the reaction product mass and catalyst bed by conventional procedures, such as distillation, without difficulty. For example, the reaction product mass may be directly distilled. Such distillation recovery procedures are well-known in the art and therefore, will not be more particularly discussed herein.

It will be realized that the starting reactants such as the lower alkanolamines can be produced in situ by the catalyzed reaction of ammonia with, for example the corresponding alkylene diol and/or epoxide. Likewise, the lower alkyleneamines can be produced from ammonia and the corresponding alkanolamine. Thus, in accordance with the instant invention, polyalkylenepolyamines can be produced from the basic materials of, for example an alkylene oxide and ammonia. Although possible, such a procedure is not preferred. It is preferred, therefore, that the desired alkanolamines and/or alkylenediamines be initially prepared, isolated and introduced into the instant process in desired quantities in accordance with the invention.

One outstanding advantage of the instant invention resides in the fact that lower alkylene polyamines after separation by, for example fractional distillation, can be returned to the reaction zone to undergo further reaction with the alkanolamines, thus producing more of the higher products. Those skilled in the art will immediately see the many ways of selectively obtaining a desired product mixture by use of reactants, reaction conditions, recycling techniques and the like.

The following examples illustrate the nature of the inventive process but are not intended to be limitative thereof. For purposes of brevity the reactant compounds employed and the products obtained are often abbreviated in the following Examples and Tables. The compound abbreviations are:

MEA—Monoethanolamine
AEEA—N-(2-aminoethyl)ethanolamine
HEP—N-(2-hydroxyethyl)piperazine EDA—Ethylenediamine
DETA—Diethylenetriamine
AEP—N-(2-aminoethyl)piperazine
TETA—Triethylenetetramine
TEPA—Tetraethylenepentamine
PEHA—Pentaethylenehexamine TETA Isomers:

NTEA—Nitrilotrisethylamine
TETA—Triethylenetetramine
DiAEP—Diaminoethylpiperazine
PEEDA—Piperazinoethylethylenediamine TEPA Isomers:

AETETA—4-Aminoethyltriethylenetetramine
TEPA—Tetraethylenepentamine
AEPEEDA—Aminoethylpiperazinoethylethylenediamine
PEDETA—Piperazinoethyldiethylenetriamine

EXAMPLE 1

A 300 ml. rocking autoclave was charged with 75 grams of ethylenediamine, 75 grams of monoethanolamine, and 15 grams of cation exchange resin Duolite ® ES-473. The autoclave was heated to 300° C. and held at this temperature for 5½ hours. The autoclave was analyzed and heavier polyamines were detected. Results are given below in Table I.

EXAMPLE 2

This run was carried out per Example 1 except the autoclave was heated to 325° C. and held at this temperature for 5 hours. The autoclave was analyzed and substantial quantities of heavier polyamines were detected. See Table I.

TABLE I

| | Feed | Example 1 | Example 2 |
|---|---|---|---|
| Lights | — | 2.1 | 3.3 |
| Water | — | 16.5 | 31.6 |
| EDA | 52.9 | 31.6 | 7.7 |
| MEA | 46.6 | 27.4 | 2.6 |
| Piperazine | 0.5 | 2.7 | 8.4 |
| DETA | — | 11.9 | 0.6 |
| AEP | — | 5.3 | 12.3 |
| Others | — | 2.0 | 10.8 |
| Heavy Amines | — | 0.5 | 22.7 |

EXAMPLE 3

Duolite ® ES-473 resin was charged to a tubular reactor with a volume of ½ liter and a hot oil jacket for heat control. A 2/1 mol ratio of EDA/MEA was continuously passed over the resin at a hot oil temperature of 305° C., a pressure of 1500 psig, and a liquid space velocity of 1 gm./hour ml. catalyst volume. The MEA conversion was 56.9% and the EDA conversion was 35.8%. The noncyclic content of the triethylenetetramine compounds was 96.8% and the noncyclic content of the tetraethylenepentamine compounds was 95.9%.

EXAMPLE 4

The same type of experiment as Example 3 was performed except that the hot oil temperature was held at 309° C. The MEA conversion was 65.8% and the EDA conversion was 36.9%. The noncyclic content of the triethylenetetramine compounds was 95.0% and the noncyclic content of the tetraethylenepentamine was 93.5%. Table II lists the reactor effluent products on a lights and water free basis.

EXAMPLE 5

By way of comparison an aluminum phosphate containing catalyst of the type disclosed in U.S. Pat. No. 4,036,881 was charged to the ½ liter continuous reactor and the same experiment was performed on the catalyst as in Example 3 except that a hot oil temperature of 325° C. was necessary to obtain the same conversion levels. As can be seen in Table II, the noncyclic content of TETA and TEPA for Example 3 and 4 are between 8 and 10% higher than this experiment with the aluminum phosphate containing catalyst.

TABLE II

| Example | MEA Conv. | EDA Conv. | Piperazine | Ethylene Glycol | Bis Amino Ethyl Ether | DETA | AEEA | AEP | HEP | TETA | % non-cyclics | TEPA | % non-cyclics | Heavy Amines | Other |
|---|---|---|---|---|---|---|---|---|---|---|---|---|---|---|---|
| 3 | 56.9 | 35.8 | 4.2 | 0.3 | 0.4 | 49.7 | 3.0 | 2.5 | 0.1 | 28.5 | 96.8 | 7.8 | 95.9 | 2.8 | 0.7 |
| 4 | 65.8 | 36.9 | 3.8 | 0.2 | 0.2 | 53.7 | 4.5 | 2.3 | 0.1 | 24.7 | 95.0 | 8.1 | 93.5 | 1.9 | 0.5 |
| 5 | 54.5 | 29.2 | 3.3 | 0.5 | 2.3 | 46.0 | 6.8 | 3.2 | 0.3 | 24.3 | 84.5 | 5.1 | 85.6 | 7.4 | 0.8 |

I claim:

1. An improved process for selectively preparing a predominantly noncyclic polyalkylene polyamine compound comprising the steps of:
    contacting an alkyleneamine compound having two primary amino groups with an alkanolamine compound having a primary amino group and a primary or secondary hydroxy group in the presence of a cation exchange resin containing active phosphorus sites acting as a catalyst at temperatures of from about 250° C. to about 400° C. under a pressure sufficient to maintain the mixture essentially in liquid phase; and
    recovering said polyalkylene polyamine compound from the resultant reaction mixture.

2. The process of claim 1 wherein said phosphorus-containing cation exchange resin contains active acid groups selected from the group consisting of phosphonous, phosphonic, phosphoric, and phosphorous groups.

3. The process of claim 2 wherein said pressure is 500-5000 psig.

4. The process of claim 3 wherein said pressure is 1000-3000 psig.

5. The process of claim 1 wherein said temperature is 295°–350° C.

6. The process of claim 4 wherein said alkanolamine compound and said alkyleneamine compound are contacted in a molar ratio of from about 2:1 to about 1:5.

7. The process of claim 5 wherein said alkanolamine is an ethanolamine of the formula:

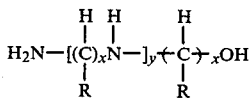

wherein R is hydrogen or lower alkyl, x is 2 and y is 0 to 3 and wherein the alkyleneamine is an ethyleneamine of the formula:

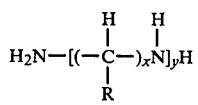

wherein R is hydrogen or lower alkyl, x is 2 and y is a number from 1 to about 4.

8. The process of claim 6 wherein said ethanolamine is monoethanolamine and wherein said ethyleneamine is ethylenediamine.

* * * * *